(12) United States Patent
Somes et al.

(10) Patent No.: US 6,168,707 B1
(45) Date of Patent: Jan. 2, 2001

(54) ION MEASUREMENT APPARATUS AND METHODS FOR IMPROVING THE ACCURACY THEREOF

(75) Inventors: Loren Somes, Dracut; Jeffrey S. Hovis, Boston; Peter F. Bronk, Medford; Robert Caporiccio, Waltham; Timothy Gillette, Brookline; Stefan Hrabosky, Pepperell, all of MA (US)

(73) Assignee: Orion Research, Inc., Beverly, MA (US)

( * ) Notice: Under 35 U.S.C. 154(b), the term of this patent shall be extended for 0 days.

(21) Appl. No.: 09/160,125

(22) Filed: Sep. 24, 1998

Related U.S. Application Data (63) Continuation-in-part of application No. 08/397,599, filed on Mar. 2, 1995, now abandoned.

(51) Int. Cl.[7] ........................... G01N 27/26; G01N 27/36
(52) U.S. Cl. ........................ 205/775; 204/400; 204/408; 204/416; 204/420; 205/787.5; 205/789.5

(58) Field of Search ........................... 204/408, 416, 204/418, 419, 420, 406, 400; 205/775, 787.5, 789, 789.5

(56) References Cited

U.S. PATENT DOCUMENTS

| 3,662,256 | 5/1972 | Eckfeldt . |
| 4,222,006 | 9/1980 | Schneider . |
| 4,321,544 | 3/1982 | Riseman . |
| 4,495,050 | 1/1985 | Ross, Jr. . |
| 4,851,104 | * 7/1989 | Connery et al. ............... 204/406 |

* cited by examiner

*Primary Examiner*—T. Tung
(74) *Attorney, Agent, or Firm*—Ernest V. Linek; Banner & Witcoff, Ltd.

(57) ABSTRACT

The accuracy and temperature-independence of ion-selective electrode meters having a logarithm resistance temperature correction incorporated therein is enhanced by using a microprocessor controlled and measured circuit with switched reference and switched capacitor filter, and by adding a linear membrane resistance term to the algorithm to improve accuracy across a wide temperature range.

17 Claims, 5 Drawing Sheets

ION MEASUREMENT APPARATUS AND METHODS FOR IMPROVING THE ACCURACY THEREOF

CROSS-REFERENCE TO RELATED APPLICATIONS

The present application is a continuation-in-part of application Ser. No. 08/397,599, filed Mar. 2, 1995, now abandoned, the disclosure of which is hereby incorporated herein by reference.

FIELD OF THE INVENTION

The invention relates to electrochemical sensors and, more particularly, to temperature-corrected electrochemical sensors characterized by an improved linearized response.

BACKGROUND OF THE INVENTION

Electrochemical sensors are used to detect the presence of ions in solution. A common form of such sensor is the well-known pH electrode which measures the concentration of $H^+$ ions in solution. Such a sensor is typically formed from a body having a membrane selectively permeable to $H^+$ ions formed or mounted on a surface thereof for immersion in, or at least contact with, a solution (or semi-solid such as meat, cheese, soil, and the like) to be measured on an exterior face thereof. A filling solution of controlled composition within the body contacts the interior of the membrane and provides a standard potential for an electrode such as a wire which is immersed in the solution. Changes in the pH of the test material (solution, etc.) to which the membrane is exposed change the potential of the electrode with respect to a reference electrode that is also in contact with the test material. The change in potential between the sensing and reference electrodes provides a direct indication of the pH of the test material.

Electrodes of this type, when used with a membrane that is specific to the ion to be measured, are also commonly used to measure other ions such as $Na^+$, $K^+$, $Ca^{2+}$, F and other mono-valent and divalent cations and anions, and are referred to generally as "ion-selective" electrodes. When available for the particular ion to be measured, such electrodes are very popular, since they usually provide a relatively fast and simple means of measurement with reasonable accuracy.

The readings provided by ion-selective electrodes, however, are strongly temperature-dependent. This is a consequence of the fact that the potential of the electrode is given by the well-known Nernst equation:

$$E = E^0 + (RT/nF) \ln a$$

where E is the potential of the electrode; $E^0$ is the standard potential of the electrode when immersed in a solution of unit activity; R is the gas constant; T is the absolute temperature; n is the charge on the ion(s); F is the Faraday constant; and a is the activity of the ion(s). Accordingly, it is essential that the readings of such electrodes be corrected for temperature.

Temperature correction is sometimes accomplished by separately measuring the temperature of the test material (e.g., solution) in which the electrode is immersed and thereafter applying a calculated correction factor to readings taken with the electrode. This is the technique used in the Eckfeldt and Scheider patents (U.S. Pat. Nos. 3,662,256 and 4,222,006). In other words, Eckfeldt and Schnieder are measuring the temperature of a test material with a separate device (i.e., thermistor) that is different from the sensing membrane (i.e., gas electrode or pH electrode). Among other drawbacks, this technique is subject to variable error arising from spatial separation between the temperature measuring element and the sensing membrane.

A more successful approach is set forth in U.S. Pat. No. 4,321,544 issued Mar. 23, 1982 to John H. Riseman for "Method And Improved Apparatus For Obtaining Temperature-Corrected Readings Of Ion Levels and Readings of Solution Temperature" and assigned to the predecessor of the present assignee. The disclosure of this patent is hereby incorporated herein by reference.

The invention described in the '544 patent (or Log R patent) makes use of the fact that the logarithm of the resistance of pH sensitive membranes varies inversely with the temperature of the material (e.g., solution) being measured. This fact is used to advantage by applying an externally-generated alternating voltage across the membrane in parallel with the DC voltage generated by the ion concentration differences across the membrane that arise from the material under test. The alternating voltage is used to measure the instantaneous resistance of the membrane and thus provide a correction factor for the measurement. This technique is referred to hereinafter as "the log R" technique.

The method described in the Log R patent was found to provide good temperature compensation above 40 degrees Celsius (40° C.). At lower temperatures, the temperature readings tend to disperse and deviate from actual temperature measurements. Temperature compensation, with the dispersant temperature values is still possible, however, the increase in temperature-dependent dispersion in the readings at least partially limits realization of the full benefits of the log R technique.

SUMMARY OF THE INVENTION

The present invention is directed to an improved linearized, temperature corrected electrochemical meter and measurement system utilizing the same. Preferably, the present invention provides an improved linearized, temperature corrected electrochemical meter that is characterized by a temperature correction factor of narrow dispersion despite the use of membranes of different types and materials and an improved log R temperature measurement system including an improved log R algorithm, an improved circuit that incorporates microprocessor control and measurement, and noise reduction techniques.

More particularly, the present invention provides an improved temperature measurement through the application of an advanced highly stable microprocessor controlled and measured circuit that doesn't require hardware calibration and is not subject to drift and through the application of a more advanced temperature correction algorithm.

It has been discovered that a temperature correction factor that is relatively linear over a wide range of temperatures and that has an unusually narrow range of dispersion despite the use of membranes of varied types and materials may be obtained from a log R type of circuitry by:

(1) establishing a target resistance-temperature (R-T) calibration curve as a function of the calibration curves of a plurality of membranes;

(2) adding a linear resistance term to the log R algorithm to correct the calculated temperature measurement made using the membrane resistance of the electrode to further linearize and provide more accuracy in the temperature correction factor across a wider temperature range;

(3) presetting the resistance-responsive circuitry of a meter capable of providing a log R response to the said target R-T calibration curve;

(4) providing a method to calibrate or adjust the resistance-response algorithm to a specific membrane material to further increase the accuracy and compensate for variations in membrane types, materials and manufacturing;

(5) use of a switched reference and switched capacitor filter to eliminate the difficult, labor intensive hardware calibrations and eliminate the troublesome hardware drift that reduces the measurement accuracy;

(6) use of a microprocessor to control and measure the sensor circuit;

(7) use of a microprocessor to eliminate hardware calibration;

(8) use of a microprocessor to implement more sophisticated temperature measurement algorithm and calibration techniques based on sensor membrane resistance; and (9) incorporating a conventional thermister temperature measurement circuit and the ability to turn off LogR to allow high accuracy "Laboratory Grade" pH measurements in the same meter that's designed to use LogR.

The target R-T calibration curve may advantageously be formed as the average of the R-T curves of spherical membranes of the type commonly used in pH and other ion-selective membranes.

BRIEF DESCRIPTION OF THE FIGURES

FIGS. 1 and 2 are graphs of the temperature of a test solution as calculated by a log R meter in the absence of the improvement of the present invention (vertical axis) as a function of the NIST thermometer measured temperature (horizontal axis) for a variety of membranes which may be used with the meter for varying applications. FIG. 1 is before temperature calibration of the algorithm, and FIG. 2 is after temperature calibration of the algorithm.

FIGS. 3 and 4 are graphs of the temperature of a test solution as calculated by a log R meter as enhanced by the present invention (vertical axis) as a function of the NIST thermometer measured temperature (horizontal axis) for the same membranes as in FIGS. 1 and 2 but showing the remarkably reduced temperature dispersion attendant on the present invention. FIG. 3 is before temperature calibration of the algorithm, and FIG. 4 is after temperature calibration of the algorithm.

DETAILED DESCRIPTION OF THE PREFERRED EMBODIMENT

The foregoing features of the present invention will be more readily understood on reference to the following detailed description of the invention when taken in connection with the above-referenced drawings.

Figure 1:
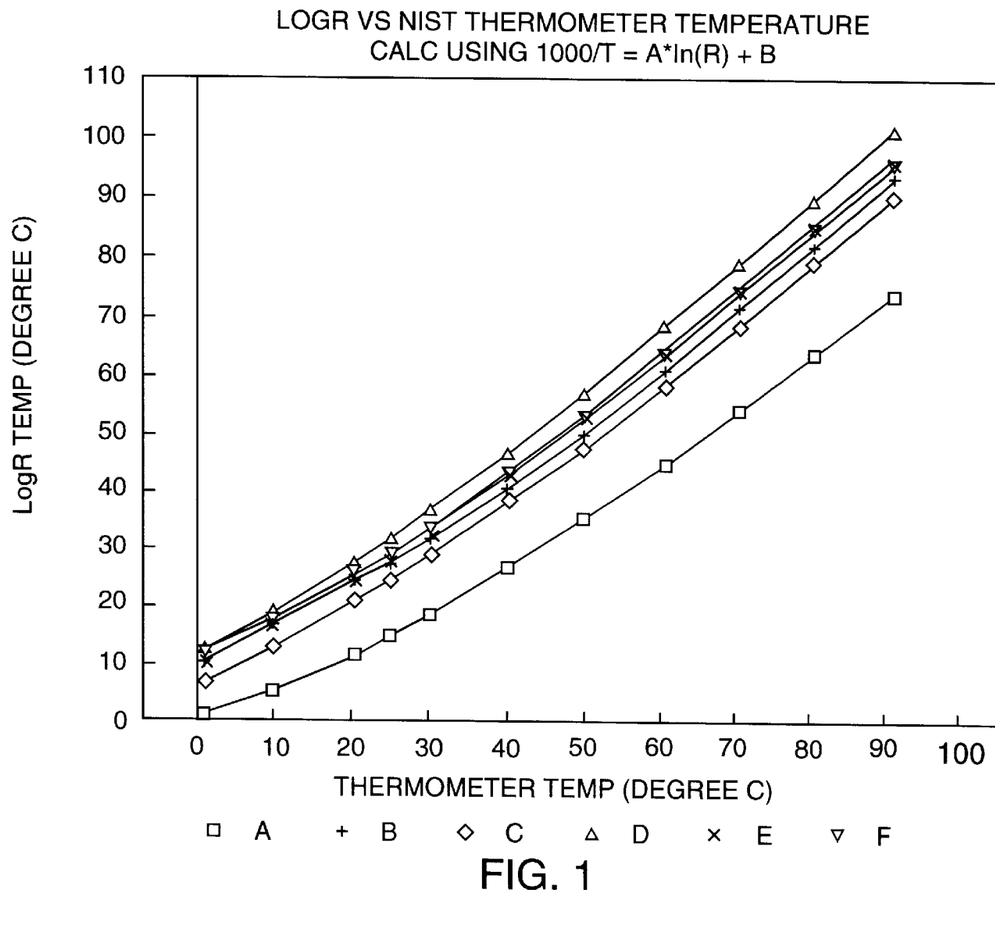
Figure 2:
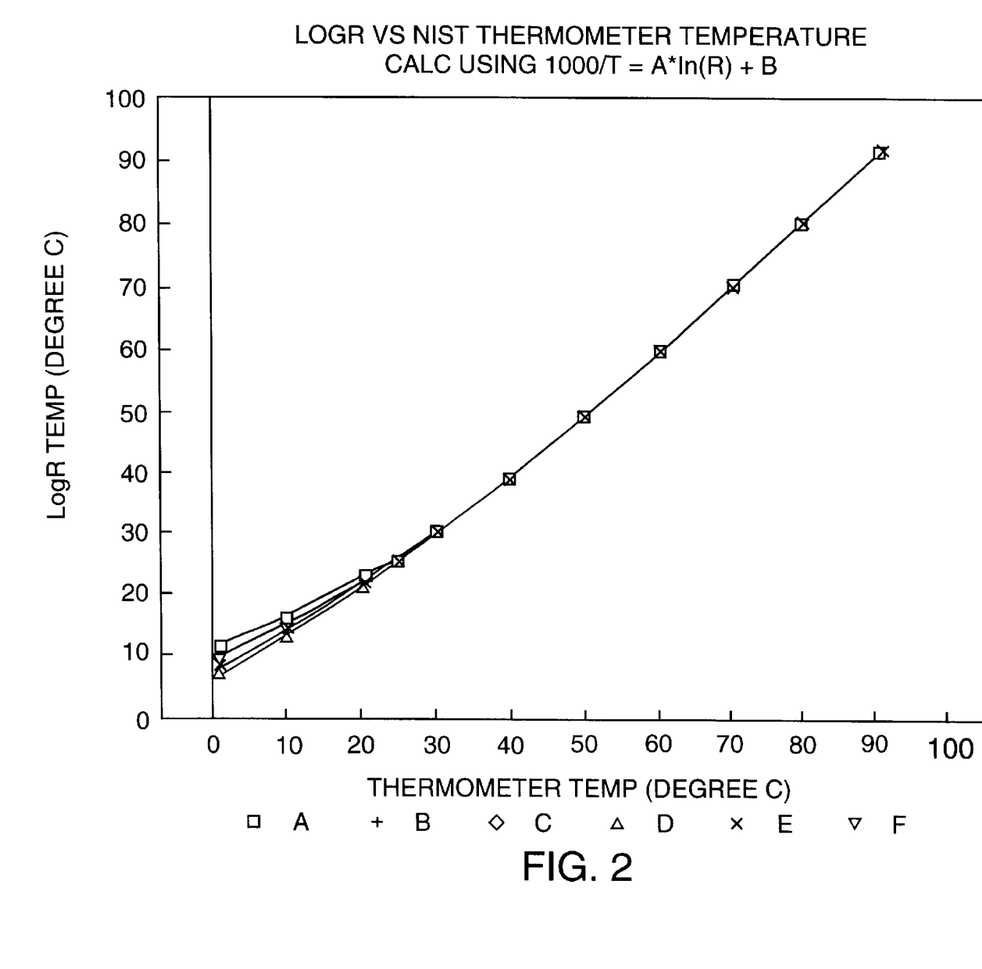
Figure 3:
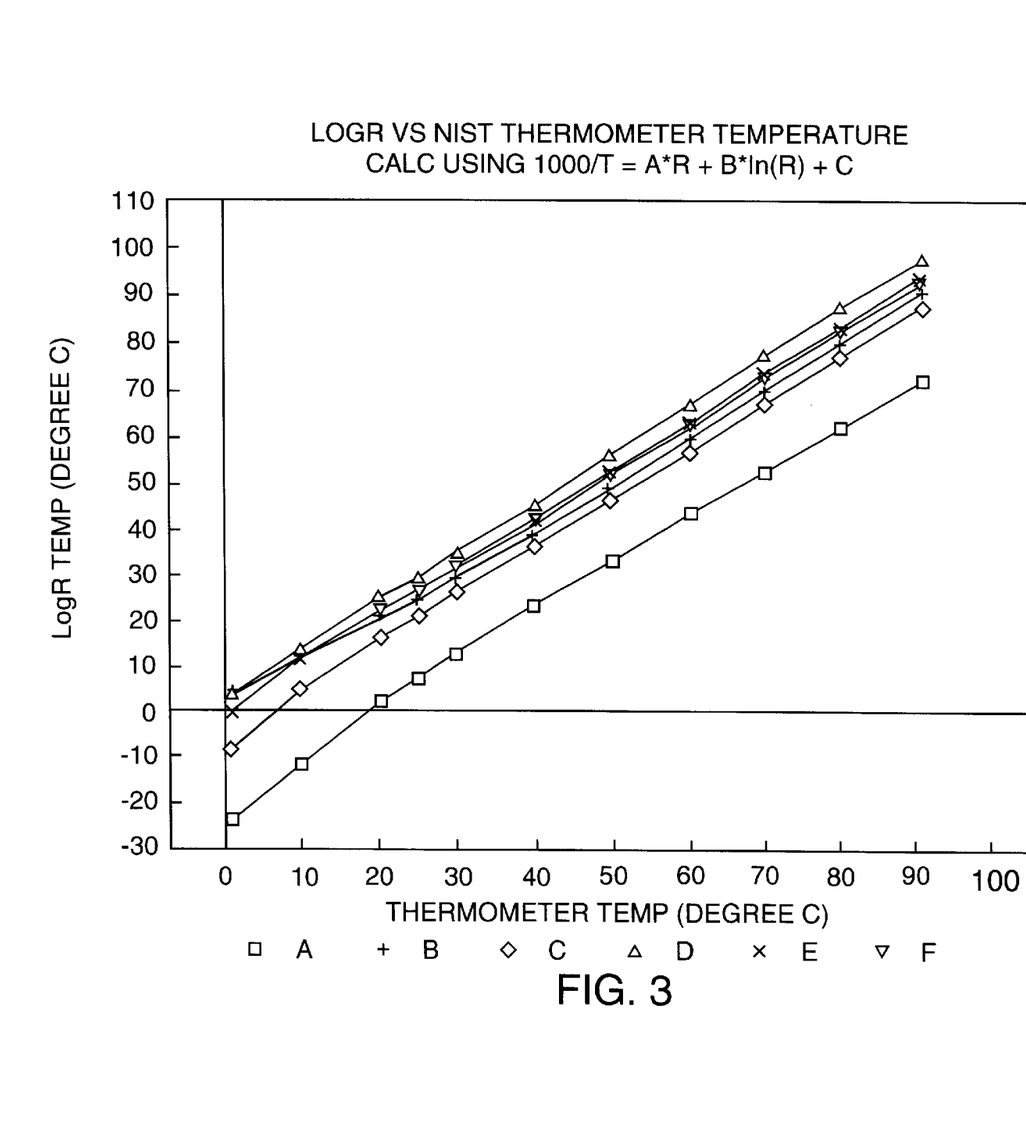

In FIG. 2, the temperature as calculated and indicated by a meter of the log R type (see U.S. Pat. No. 4,321,544 supra) for ion-selective electrodes using six different membranes, A, B, C, D, E, and F respectively, is shown as compared to the temperature measured by a NIST certified thermometer.

Above about forty degrees Celsius (40° C.), the calibration curves of the individual electrodes using the prior art log R algorithm are essentially undistinguishable. Below about 40° C., the curves are more readily seen to disperse.

Although the slopes of the temperature curves are fairly linear and similar over the temperature range of interest (about 0° C. to about 90° C.) in FIG. 2, the temperature calculated by the log R meter for a given solution may vary by as much as about 15° C. from the actual solution temperature at the electrodes and the potential correction computed from the Nernst equation with these data will vary accordingly. This has heretofore constrained the utilization of such a meter with a variety of electrodes, over a wide temperature range. In particular, this limited the application of this technique in the most important and commonly used region of room temperature (~25° C.).

Figure 4:
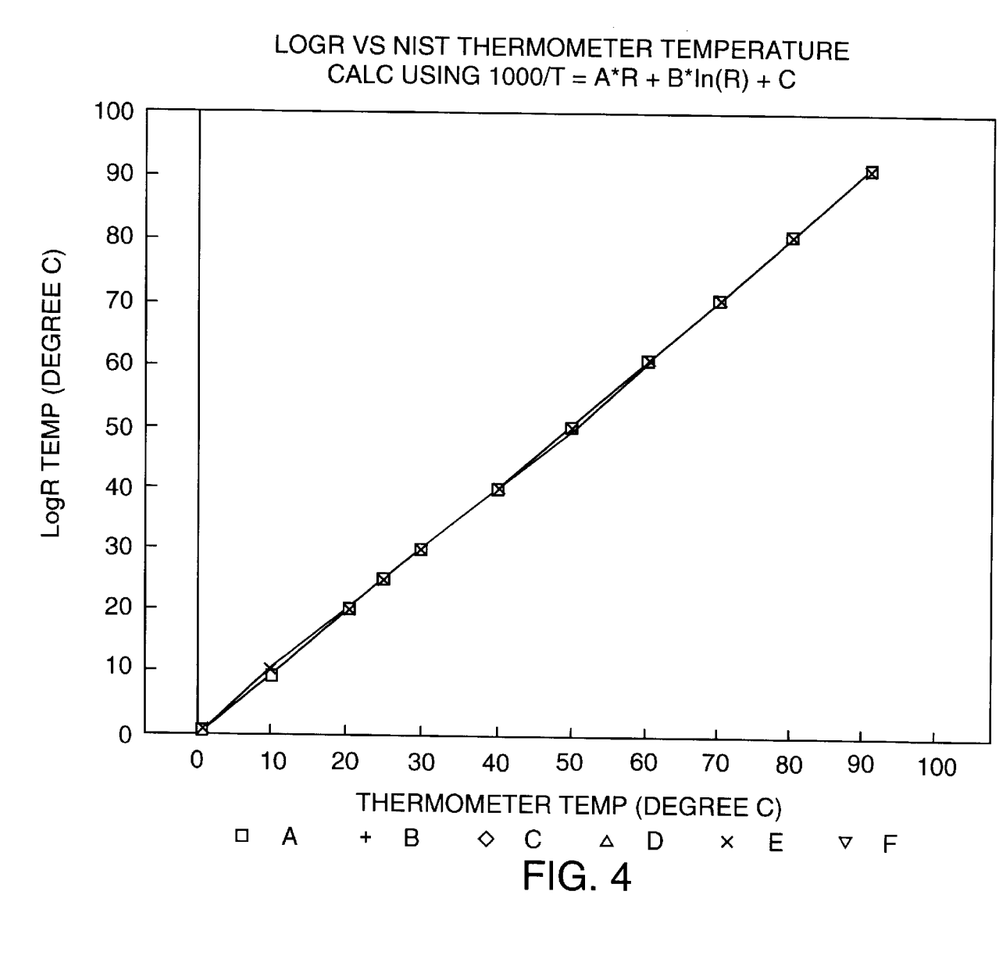

FIG. 4 shows the remarkable reduction, and near elimination, of the temperature dispersion for the same electrodes as in FIG. 2, as a consequence of implementation of the present invention. In other words, now, over a wide range of temperatures, an improved log R meter, adjusted to the target calibration curve, and further calibrated to an individual electrode, will provide a response that is essentially independent of the particular electrode type and manufacturing variations. The present invention thus greatly expands the usefulness of the log R type meters.

The present invention will be further illustrated with reference to the following examples which aid in the understanding of the present invention, but which are not to be construed as limitations thereof. All temperatures are expressed in degrees Celsius.

EXAMPLES

The optimum electrode resistance for Log R performance between about 0° and 100° C. is from 50 to 300 Megohms at 25° C. These resistance limits are based on electrical limits of measurement based on the electrodes cable capacitance and reference electrode impedance. At higher or lower resistances some reduction in accuracy occurs at the ends of the temperature range. For instance at higher resistance the accuracy begins to degrade when the temperature approaches 0° C. and with lower resistances the accuracy begins to degrade when the temperature approaches 100° C. Testing has shown that acceptable accuracy across the full temperature range can still be achieved with electrode resistances that are over three times higher and two-thirds lower than the optimal. In fact no overall reduction in accuracy was detected, but in order to achieve this accuracy at these higher and lower resistances, it was necessary to employ noise reduction methods in both the hardware and the software. Accuracy may also be impacted by the choice of calibration method (one, two or three point). Optimum measurements are achieved when measurements are made within the calibration bracketed temperature range.

The following tables (1–3) illustrate the scope and details of the measurements which entail the present invention.

TABLE 1

One Point Log R Calibration Maximum Measured Temperature Compensation pH Error At 3 & 11 pH

| Electrode units | Max Temp Error 20–30° C. ° C. | Max Temp Error 30–50° C. ° C. | Max Temp Comp pH Error 20–30° C. ° C. | Max Temp Comp pH Error 30–50° C. ° C. | Minimum Resistance @ 100° C. Megohms | Maximum Resistance @ 0° C. Megohms | Average Resistance @ 25° C. Megohms |
|---|---|---|---|---|---|---|---|
| 8202 | 0.19 | 0.10 | 0.002 | 0.001 | 1.95 | 2153.67 | 327.85 |
| 8203 | 0.42 | 0.31 | 0.005 | 0.004 | 1.56 | 924.52 | 198.22 |
| 8235 | 1.52 | 1.71 | 0.018 | 0.021 | 7.80 | 3843.09 | 945.92 |
| 8256 | 0.13 | 0.18 | 0.002 | 0.002 | 1.34 | 1602.28 | 252.01 |
| 8272 | 0.79 | 0.79 | 0.009 | 0.009 | 1.21 | 1211.45 | 186.24 |
| 9202 | 0.62 | 0.54 | 0.007 | 0.006 | 1.75 | 2105.62 | 320.14 |
| 9203 | 0.21 | 0.32 | 0.003 | 0.004 | 0.84 | 1104.15 | 140.58 |
| 9206 | 0.36 | 0.40 | 0.004 | 0.005 | 1.67 | 1923.17 | 293.42 |
| 9207 | 0.65 | 0.58 | 0.008 | 0.007 | 2.21 | 1134.60 | 284.71 |
| 9256 | 0.40 | 0.32 | 0.005 | 0.004 | 1.36 | 2540.45 | 324.40 |
| 9272 | 0.24 | 0.39 | 0.003 | 0.005 | 1.31 | 1311.73 | 172.36 |

30–50° C. Column Is Good For All 20° C. Ranges Above 30° C.
One Point Calibrations were Performed In The Center of Each Range.
Do Not Use Single Point Calibrations When Measuring Below 20° C.

TABLE 2

Two Point Log R Calibration Maximum Measured Temperature COmpensation pH Error At 3 & 11 pH. 20–40° C. Column Is Good For All 20° C. Ranges Above 20° C.

| Electrode units | Max Temp Error 0–25° C. ° C. | Max Temp Error 20–40° C. ° C. | Max Temp Comp pH Error 0–25° C. ° C. | max Temp Comp Ph Error 20–40° C. ° C. | Minimum Resistance @ 100° C. Megohms | Maximum Resistance @ 0° C. Megohms | Average Resistance @ 25° C. Megohms |
|---|---|---|---|---|---|---|---|
| 8202 | 0.36 | 0.10 | 0.004 | 0.001 | 1.95 | 2153.67 | 327.85 |
| 8203 | 0.33 | 0.03 | 0.004 | 0.000 | 1.56 | 924.52 | 198.22 |
| 8235 | 0.05 | 0.33 | 0.001 | 0.004 | 7.80 | 3843.09 | 945.92 |
| 8256 | 0.75 | 0.16 | 0.009 | 0.002 | 1.34 | 1602.28 | 252.01 |
| 8272 | 0.82 | 0.13 | 0.010 | 0.002 | 1.21 | 1211.45 | 186.24 |
| 9202 | 1.01 | 0.23 | 0.012 | 0.003 | 1.75 | 2105.62 | 320.14 |
| 9203 | 0.53 | 0.23 | 0.006 | 0.003 | 0.84 | 1104.15 | 140.58 |
| 9206 | 0.94 | 0.31 | 0.011 | 0.004 | 1.67 | 1923.17 | 293.42 |
| 9207 | 0.29 | 0.16 | 0.003 | 0.002 | 2.21 | 1134.60 | 284.71 |
| 9256 | 0.63 | 0.06 | 0.008 | 0.001 | 1.36 | 2540.45 | 324.40 |
| 9272 | 0.62 | 0.16 | 0.007 | 0.002 | 1.31 | 1311.73 | 172.36 |

TABLE 3

Three Point Log R Calibration Maximum Measured Temperature Compensation pH Error At 3 & 11 pH

| Electrode units | Max Temp Error 0–25° C. ° C. | Max Temp Error 20–40° C. ° C. | Max Temp Comp pH Error 0–25° C. ° C. | Max Temp Comp pH Error 20–40° C. ° C. | Minimum Resistance @ 100° C. Megohms | Maximum Resistance @ 0° C. Megohms | Average Resistance @ 25° C. Megohms |
|---|---|---|---|---|---|---|---|
| 8202 | 0.12 | 0.23 | 0.001 | 0.003 | 1.95 | 2153.67 | 327.85 |
| 8203 | 0.11 | 0.04 | 0.001 | 0.000 | 1.56 | 924.52 | 198.22 |
| 8235 | 0.11 | 0.14 | 0.001 | 0.002 | 7.80 | 3843.09 | 945.92 |
| 8256 | 0.14 | 0.42 | 0.002 | 0.005 | 1.34 | 1602.28 | 252.01 |
| 8272 | 0.15 | 0.06 | 0.002 | 0.001 | 1.21 | 1211.45 | 186.24 |
| 9202 | 0.11 | 0.16 | 0.001 | 0.002 | 1.75 | 2105.62 | 320.14 |
| 9203 | 0.09 | 0.32 | 0.001 | 0.004 | 0.84 | 1104.15 | 140.58 |
| 9206 | 0.25 | 0.27 | 0.003 | 0.003 | 1.67 | 1923.17 | 293.42 |
| 9207 | 0.04 | 0.05 | 0.000 | 0.001 | 2.21 | 1134.60 | 284.71 |

TABLE 3-continued

Three Point Log R Calibration Maximum Measured Temperature Compensation pH Error At 3 & 11 pH

| Electrode units | Max Temp Error 0–25° C. ° C. | Max Temp Error 20–40° C. ° C. | Max Temp Comp pH Error 0–25° C. ° C. | Max Temp Comp pH Error 20–40° C. ° C. | Minimum Resistance @ 100° C. Megohms | Maximum Resistance @ 0° C. Megohms | Average Resistance @ 25° C. Megohms |
|---|---|---|---|---|---|---|---|
| 9256 | 0.31 | 0.42 | 0.004 | 0.005 | 1.36 | 2540.45 | 324.40 |
| 9272 | 0.11 | 0.02 | 0.001 | 0.000 | 1.31 | 1311.73 | 172.36 |

20–40° C. Column Is Good For All 20° C. Ranges Above 20° C.

Log R Test Data Analysis, Tolerance Analysis, and Drift Analysis Using a Thermistor Based Temperature Reference Eleven electrode models (3–4 of each) were tested at 15 temperatures, ranging from 0–90° C. The testing sequence was conducted with both increasing and decreasing temperature steps to test for hysteresis and the tests were repeated after 2 and 4 week periods to test for and evaluate drift. In addition testing was conducted in various buffers (4, 7, and 10 pH) to determine if there were any pH interferences on the membranes temperature response. The test instrumentation consisted of a 6 channel measuring circuit using an AC signal superimposed on the DC potential generated by the electrode. The circuit was designed to reject the out of phase components of the AC signal measured to eliminate inductive or capacitive effects of the system (In a micro based instrument this could also be accomplished by measuring the capacitance of the electrode/ system and eliminating it in software). This circuit was connected to a computerized data logging system, which recorded the AC signal current and voltage across the membrane in response to temperature. This system also recorded independent temperature measurement with a thermistor based temperature probe. The electrodes were connected to this test setup and immersed in temperature controlled baths containing pH buffer. Based on the resulting test data it was found that the following equation best fit the electrodes Log R temperature response:

$$1000/T = A*R + B*\ln(R) + C \qquad \text{(Equation 1)}$$

Where:
T=degrees (°) Kelvin
R=Membrane Resistance
A, B & C=Calibration Values

System Defaults:
A=0.000099
B=0.11964
C=2.652662

The 1000 in the 1000 over T is a scaling factor and is not a fundamental part of the mathematical relationship. The default values were an average of the typical calibration values measured for the electrode models used in the testing. Previously, in U.S. Pat. No. 4,321,544, it had been shown that the temperature on an electrodes membrane was inversely proportional to the logarithm of the membranes resistance (this equation is shown below):

$$1/T = A*\ln(R) + B \qquad \text{(Equation 2)}$$

Where:
T=Temperature in degrees (°) Kelvin
R=Membrane Resistance
A & B=Calibration Constants It was further shown by this prior art that the electrode membrane resistance could be measured within the system by superimposing an AC signal on the DC potential generated by the electrode in the sample solution. However, equation 2 does not accurately describe the electrode's temperature response across the entire temperature range. Analysis by the present inventors showed that the electrode/ system had an inverse linear relationship of the membrane resistance to temperature in addition to the inverse logarithmic relation to temperature defined in the prior art. It also showed that this linear relationship was insignificant above 40° C., but was very significant at lower temperatures. This resulted in equation 1 shown above. This new model increased the low temperature accuracy in temperature determination using membrane resistance by up to twenty (20) times.

In addition to the new model described above, the present inventors also found that the effect of the linear relationship could be reduced by replacing the 1/T term in the prior art model as shown below:

$$T = A*\ln(R) + B \qquad \text{(Equation 3)}$$

Where:
T=Temperature in Degrees Kelvin (° K)
R=Membrane Resistance
A & B=Calibration Constants This equation increases the error over the full range but does provide better temperature response at the lower temperatures without taking into account the linear relationship of membrane resistance to temperature. Both equations 1 and 3 are significant improvements over the prior art equation 2. Equation 1 has the best accuracy, but equation 3 requires only two (2) calibration points for its maximum accuracy versus the three (3) calibration points needed with equation 1 for its maximum accuracy. The remaining tables (infra) and FIGS. 1–4 illustrate the results of each of the three models described above.

In addition to defining a new model of the membrane resistance to temperature relationship the present inventors were able to determine from the test data that the membrane resistance was unaffected by solution pH and that there was no hysteresis in the membrane temperature response. The testing also showed that the electrodes Log R temperature response drift was less than 0.1° C. per week. This drift was primarily in the "A" coefficient of equation 1, and primarily effected the low temperature (below 40° C.) response.

Description of the Improved Log R System Measuring Technique

The measurement technique employed is similar to that of U.S. Pat. No. 4,321,544 (Riseman), except the new circuit design is a major improvement over the prior art described in the '544 patent (or LogR patent). The '544 patent described an analog circuit, which limited the sophistication of the temperature measurement algorithms and calibration techniques, which could be implemented. In addition the circuit described in the '544 was difficult to calibrate and subject to calibration drift, which increase the measurement error. The key advantages of the present invention over the '544 patent are:

(1) The new hardware design described in this invention is microprocessor based which allows the use of the more sophisticated temperature measurement and calibration algorithms to dramatically improve the temperature measurement and compensation performance.

(2) In addition the use of a switched reference and switched capacitor filter with a microprocessor eliminates the difficult, labor intensive hardware calibrations and provides a much more stable circuit. All the hardware calibration is performed in software in this circuit design.

(3) This design also allows the LogR circuitry to be turned off, and contains circuitry for using conventional thermister temperature measurement for temperature compensation. This improves the pH signal stability for high resolution and accuracy pH readings.

Additional advantages include the following:

A. It is possible to impose an AC voltage of considerable amplitude to a glass electrode without disturbing the electrode's DC output voltage.

B. The resistance of the electrode glass is very temperature dependent, with the resistance decreasing by about a factor of 2 for every 10° C. Therefore, measuring the resistance by the application of AC voltage allows the determination of temperature without interferences with measurement of the DC electrode voltage that indicates ion activity.

C. Both temperature and ion activity can thus be measured by a single electrode. Furthermore, the temperature so measured is directly relevant to temperature correction of the ion activity measurement.

Figure 5:
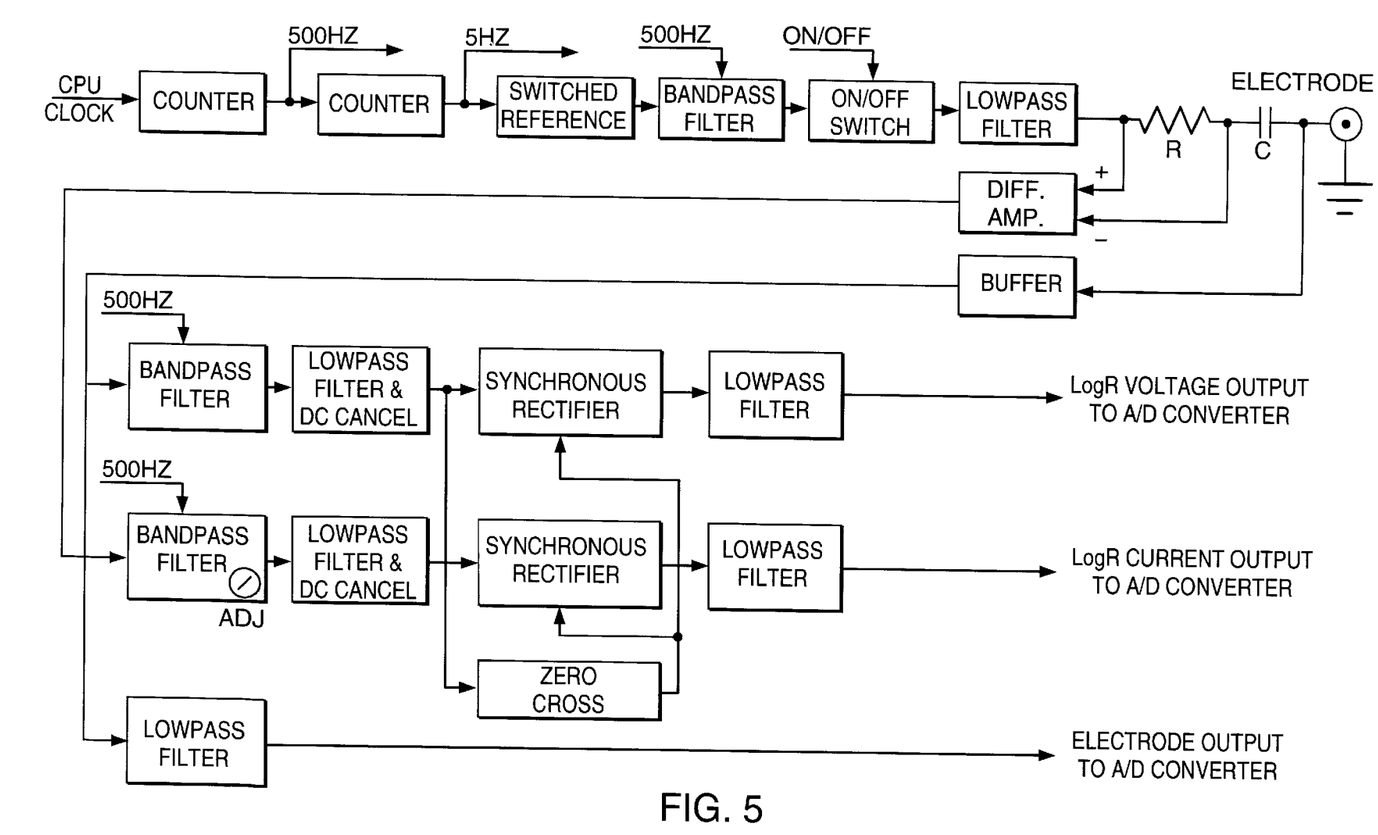
FIG. 5 is a block diagram of the new and improved log R system as discussed in the examples.

Block Diagram (see FIG. 5)

FIG. 5 is a block diagram of the Improved Log R System, which should be referred to for the discussion that follows:

AC Voltage Generation

A sinusoidal voltage of stable amplitude and frequency is used to measure the electrode resistance. For the improved system 5 Hz was selected to minimize interference from 50 Hz and 60 Hz power. The minimization occurs because each half cycle of 5 Hz contains an integral number of cycles of 50 Hz or 60 Hz. The frequency is produced with two counters directly from the crystal oscillator of the microprocessor. A switched reference gives a 5 Hz square wave of known amplitude. This is fed to a switched capacitor bandpass filter whose output is a stepped approximation of a sinusoid. The bandpass filter output goes to an on/off switch that allows the computer system to inject Log R drive voltage or not depending on the instrument operating mode. The on/off switch feeds a lowpass filter that removes the steps produced by the bandpass filter and outputs a stable sinusoidal drive signal.

AC Voltage Injection

The sinusoidal signal drive signal is fed into the electrode by means of a resistor, R and capacitor C. The capacitor prevents the low impedance and DC voltage of the lowpass filter from affecting the DC output of the electrode. The function of the resistor is described below.

Measuring Electrode Impedance

The impedance of an electrode has two predominant terms:

A. The resistance of the electrode, which is the measurement of interest.

B. The parallel capacitance of the electrode and its cable, which is information to be ignored.

Fortunately, it is possible to separate these elements because the current through the resistance is in phase with the voltage across it whereas the current through the capacitance is 90° out of phase with the voltage across it. The total voltage on the electrode is measured at the output of a high input impedance buffer. The voltage consists of two signals:

A. The DC output voltage of the electrode.

B. The AC voltage imposed by the sinusoidal drive voltage, R, and C.

Measuring the voltage across R gives the total current into the electrode. The part of the total current that is in phase with the electrode voltage is used to determine the electrode resistance. The part of the total current that is out of phase is ignored.

Voltage and Current Signal Filtering

The voltage and current signals for measuring the electrode resistance are processed through two identical filter channels.

A. The two bandpass filters reduce noise and eliminate DC voltage. The current channel filter has a slight amount of adjustment to equalize the phase shift between the voltage and current channels. These are switched capacitor filters that produce stepped sinusoids as described above.

B. The lowpass filters that follow eliminates the steps from the bandpass filters. They are of a somewhat unusual configuration that also cancels any DC voltage output from the bandpass filters.

Zero Cross and Synchronous Rectifiers

A highly sensitive circuit is used to determine the zero crossing of the voltage channel. Its output is used to synchronously rectify the voltage and current channels. The output of the voltage channel rectifier is a full wave rectified sinusoid, which has a DC average value. The output of the current channel rectifier has two parts:

A. A full wave rectified sinusoid which has a DC average value. This is the resistive part of the electrode impedance.

B. A rectification of the out of phase component which has no DC average value. This is the capacitive part of the electrode impedance which we wish to ignore.

Final Outputs

Three lowpass filters are used to supply inputs to the Analog to Digital Converter. Two filters get rid of the AC components of the Log R voltage and current synchronous rectifiers described above. A third extracts the DC electrode voltage from the electrode input buffer by removing the 5 Hz signal.

Test data for 11 models (3–4 each) of electrodes at 15 temperatures, ranging from 0° to 90° C. have been evaluated. Based on these data it was found that the following equation best fit the electrodes Log R temperature response:

$$1000/T = A*R + B*\ln(R) + C$$

Where:
T=degrees (°) Kelvin
R=Membrane Resistance
A, B & C=Calibration Values

System Defaults:
A=0.000099
B=0.11964
C=2.652662

Using this equation with a 3 point calibrations at various temperatures for the A, B & C values, the following data tables (4 & 5) were obtained from a comparison of the calculated temperature to the thermistor measured values.

TABLE 4

| Temp. error ° C. | | 8235 | 9207 | 8202 | 8272 | 8256 | 9256 | 9202 | 9203 | 9206 | 9272 | 8203 |
|---|---|---|---|---|---|---|---|---|---|---|---|---|
| Calibrated at 0, 25, & 90° C.: | | | | | | | | | | | | |
| Max | | 0.24 | 0.41 | 1.11 | 0.32 | 0.88 | 0.63 | 0.40 | 0.44 | 0.98 | 0.36 | 0.31 |
| Avg | | 0.10 | 0.13 | 0.48 | 0.13 | 0.38 | 0.21 | 0.14 | 0.18 | 0.47 | 0.14 | 0.11 |
| Std | | 0.12 | 0.17 | 0.58 | 0.15 | 0.47 | 0.29 | 0.17 | 0.22 | 0.54 | 0.18 | 0.14 |
| Temp. Error (° C.) | AVG | | | | | | | | | | | |
| Max | 0.55 | | | | | | | | | | | |
| Mean | 0.22 | | | | | | | | | | | |
| Std Dev | 0.27 | | | | | | | | | | | |
| Calibrated at 0, 10 & 25° C.: | | | | | | | | | | | | |
| Max | | 0.11 | 0.04 | 0.15 | 0.05 | 0.15 | 0.09 | 0.03 | 0.06 | 0.18 | 0.01 | 0.11 |
| Avg | | 0.07 | 0.02 | 0.05 | 0.01 | 0.05 | 0.04 | 0.02 | 0.02 | 0.07 | 0.01 | 0.04 |
| Std | | 0.03 | 0.02 | 0.07 | 0.02 | 0.07 | 0.05 | 0.01 | 0.03 | 0.07 | 0.01 | 0.05 |
| Temp. Error (° C.) | AVG | | | | | | | | | | | |
| Max | 0.09 | | | | | | | | | | | |
| Mean | 0.04 | | | | | | | | | | | |
| Std Dev | 0.04 | | | | | | | | | | | |

TABLE 5

The original data was then re-analyzed using a 2 point calibration to correct for drift.

Calibrated at 20, 25 & 40° C.

| Temp. error ° C. | | 8235 | 9207 | 8202 | 8272 | 8256 | 9256 | 9202 | 9203 | 9206 | 9272 | 8203 |
|---|---|---|---|---|---|---|---|---|---|---|---|---|
| Max | | 0.14 | 0.05 | 0.02 | 0.03 | 0.05 | 0.02 | 0.02 | 0.01 | 0.11 | 0.04 | 0.04 |
| Avg | | 0.06 | 0.02 | 0.01 | 0.01 | 0.02 | 0.01 | 0.01 | 0.00 | 0.05 | 0.01 | 0.01 |
| Std | | 0.08 | 0.02 | 0.00 | 0.02 | 0.03 | 0.02 | 0.01 | 0.00 | 0.04 | 0.02 | 0.02 |
| Temp. Error (° C.) | AVG | | | | | | | | | | | |
| Max | 0.05 | | | | | | | | | | | |
| Mean | 0.02 | | | | | | | | | | | |
| Std Dev | 0.02 | | | | | | | | | | | |

Test data for the following 9 models (1 each) of electrodes (Orion Model Nos. 8202, 8235, 8256, 8272, 9202, 9203, 9206, 9207 and 9256) were obtained and evaluated at 15 temperatures, ranging from 0° to 90° C. These electrodes were retested 7 weeks later for Model Nos. 8235, 9207, 8202, 8272, & 8256, and 5 weeks later for Model Nos. 9256, 9202, 9203, & 9206. The retest results were used to perform a 1, 2 and 3 point calibration. Below are tables (6–15) of the original data using the 1, 2 and 3 point calibrations obtained from the retest. As can be seen there was very little drift over this 5–7 week period. The drift was approximately 0.1° C. per week.

TABLE 6

DRIFT RESULTS OVER 5–7 WEEKS

| Temp. error (° C.) | 8235 | 9207 | 8202 | 8272 | 8256 | 9256 | 9202 | 9203 | 9206 | AVG |
|---|---|---|---|---|---|---|---|---|---|---|
| Calibrated at 0, 25 & 90° C.: | | | | | | | | | | |
| Max | 1.63 | 0.55 | 0.83 | 0.79 | 1.17 | 1.87 | 0.63 | 1.42 | 1.05 | 1.10 |
| Mean | 0.47 | 0.23 | 0.37 | 0.24 | 0.46 | 0.73 | 0.26 | 0.41 | 0.48 | 0.40 |
| Std Dev | 0.56 | 0.21 | 0.45 | 0.24 | 0.55 | 0.63 | 0.31 | 0.52 | 0.56 | 0.45 |
| Calibrated at 0, 10 & 25° C.: | | | | | | | | | | |
| Max | 0.51 | 0.31 | 0.22 | 0.53 | 0.65 | 1.22 | 0.59 | 1.39 | 0.44 | 0.65 |
| Mean | 0.32 | 0.18 | 0.13 | 0.41 | 0.33 | 0.87 | 0.19 | 0.79 | 0.25 | 0.39 |
| Std Dev | 0.36 | 0.21 | 0.14 | 0.12 | 0.20 | 0.22 | 0.28 | 0.42 | 0.12 | 0.23 |
| Calibrated at 20, 25 & 40° C.: | | | | | | | | | | |
| Max | 0.44 | 0.29 | 0.32 | 0.43 | 0.29 | 0.73 | 0.25 | 0.63 | 0.28 | 0.40 |
| Mean | 0.24 | 0.23 | 0.20 | 0.38 | 0.23 | 0.53 | 0.14 | 0.35 | 0.19 | 0.28 |
| Std Dev | 0.13 | 0.06 | 0.07 | 0.07 | 0.04 | 0.20 | 0.16 | 0.19 | 0.09 | 0.11 |

TABLE 7

The original data was then re-analyzed using a 2 point calibration to correct for drift.

| Temp. error (° C.) | 8235 | 9207 | 8202 | 8272 | 8256 | 9256 | 9202 | 9203 | 9206 | AVG |
|---|---|---|---|---|---|---|---|---|---|---|
| Calibrated at 0 & 90° C.: | | | | | | | | | | |
| Max | 1.09 | 0.37 | 1.03 | 0.53 | 0.94 | 1.67 | 0.79 | 0.89 | 1.05 | 0.93 |
| Mean | 0.50 | 0.16 | 0.37 | 0.19 | 0.31 | 0.84 | 0.31 | 0.32 | 0.54 | 0.39 |
| Std Dev | 0.55 | 0.20 | 0.49 | 0.15 | 0.31 | 0.61 | 0.37 | 0.32 | 0.52 | 0.39 |
| Calibrated at 0 & 25° C.: | | | | | | | | | | |
| Max | 0.05 | 0.23 | 0.14 | 0.21 | 0.11 | 0.07 | 0.37 | 0.23 | 0.14 | 0.17 |
| Mean | 0.03 | 0.12 | 0.06 | 0.10 | 0.06 | 0.04 | 0.17 | 0.12 | 0.08 | 0.09 |
| Std Dev | 0.01 | 0.09 | 0.07 | 0.08 | 0.06 | 0.04 | 0.15 | 0.09 | 0.08 | 0.07 |
| Calibrated at 20 & 40° C.: | | | | | | | | | | |
| Max | 0.28 | 0.08 | 0.17 | 0.15 | 0.08 | 0.40 | 0.50 | 0.37 | 0.12 | 0.24 |
| Mean | 0.11 | 0.05 | 0.06 | 0.06 | 0.05 | 0.20 | 0.17 | 0.15 | 0.06 | 0.10 |
| Std Dev | 0.11 | 0.05 | 0.06 | 0.07 | 0.02 | 0.14 | 0.18 | 0.18 | 0.07 | 0.10 |

TABLE 8

Next 3 of each electrode was tested to check for consistency. The following tables shows the results with 3 point calibrations.

| Calibrated at 0, 25 & 90° C.: | | | | | | | | |
|---|---|---|---|---|---|---|---|---|
| Temp. error (° C.) | 9202 | 9202 | 9202 | AVG | 9206 | 9206 | 9206 | AVG |
| Max | 0.67 | 0.73 | 0.92 | 0.77 | 0.63 | 1.11 | 0.71 | 0.82 |
| Mean | 0.32 | 0.20 | 0.40 | 0.31 | 0.27 | 0.53 | 0.29 | 0.26 |
| Std Dev | 0.37 | 0.27 | 0.49 | 0.38 | 0.31 | 0.56 | 0.37 | 0.41 |

| Calibrated at 0, 25 & 90° C.: | | | | | | | | |
|---|---|---|---|---|---|---|---|---|
| Temp. error (° C.) | 8272 | 8272 | 8272 | AVG | 9272 | 9272 | 9272 | AVG |
| Max | 0.85 | 0.60 | 0.87 | 0.77 | 0.48 | 0.47 | 0.45 | 0.47 |
| Mean | 0.37 | 0.22 | 0.37 | 0.32 | 0.27 | 0.19 | 0.10 | 0.18 |
| Std Dev | 0.43 | 0.28 | 0.46 | 0.39 | 0.29 | 0.23 | 0.15 | 0.22 |

| Calibrated at 0, 25 & 90° C.: | | | | | | | | |
|---|---|---|---|---|---|---|---|---|
| Temp. error (° C.) | 9203 | 9203 | 9203 | AVG | 8202 | 8202 | 8202 | AVG |
| Delta | 0.73 | 0.52 | 0.52 | 0.59 | 0.70 | 0.72 | 0.78 | 0.73 |
| Mean | 0.22 | 0.11 | 0.16 | 0.16 | 0.26 | 0.36 | 0.28 | 0.30 |
| Std Dev | 0.27 | 0.18 | 0.22 | 0.22 | 0.33 | 0.43 | 0.35 | 0.37 |

TABLE 9

| Calibrated at 0, 25 & 90° C.: | | | | | | | | |
|---|---|---|---|---|---|---|---|---|
| Temp. error (° C.) | 8256 | 8256 | 8256 | AVG | 9256 | 9256 | 9256 | AVG |
| Max | 1.46 | 1.01 | 1.61 | 1.36 | 1.44 | 1.89 | 1.37 | 1.57 |
| Mean | 0.61 | 0.35 | 0.69 | 0.55 | 0.59 | 0.81 | 0.55 | 0.65 |
| Std Dev | 0.57 | 0.37 | 0.68 | 0.54 | 0.58 | 0.75 | 0.61 | 0.65 |

TABLE 9-continued

| Calibrated at 0, 10 & 25° C.: | | | | | | | | |
|---|---|---|---|---|---|---|---|---|
| Temp. error (° C.) | 9202 | 9202 | 9202 | AVG | 9206 | 9206 | 9206 | AVG |
| Max | 0.02 | 0.06 | 0.11 | 0.06 | 0.13 | 0.25 | 0.08 | 0.15 |
| Mean | 0.01 | 0.02 | 0.04 | 0.02 | 0.05 | 0.08 | 0.04 | 0.06 |
| Std Dev | 0.00 | 0.03 | 0.05 | 0.03 | 0.05 | 0.10 | 0.30 | 0.06 |

| Calibrated at 0, 10 & 25° C.: | | | | | | | | |
|---|---|---|---|---|---|---|---|---|
| Temp. error (° C.) | 8272 | 8272 | 8272 | AVG | 9272 | 9272 | 9272 | AVG |
| Max | 0.04 | 0.01 | 0.15 | 0.07 | 0.07 | 0.11 | 0.11 | 0.10 |
| Mean | 0.02 | 0.01 | 0.06 | 0.03 | 0.03 | 0.03 | 0.03 | 0.03 |
| Std Dev | 0.01 | 0.00 | 0.06 | 0.02 | 0.04 | 0.04 | 0.05 | 0.04 |

TABLE 10

| Calibrated at 0, 10 & 25° C.: | | | | | | | | |
|---|---|---|---|---|---|---|---|---|
| Temp. error (° C.) | 9203 | 9203 | 9203 | AVG | 8202 | 8202 | 8202 | AVG |
| Max | 0.09 | 0.08 | 0.02 | 0.06 | 0.04 | 0.12 | 0.06 | 0.07 |
| Mean | 0.04 | 0.03 | 0.01 | 0.03 | 0.03 | 0.04 | 0.04 | 0.03 |
| Std Dev | 0.05 | 0.03 | 0.01 | 0.03 | 0.01 | 0.06 | 0.02 | 0.03 |

| Calibrated at 0, 10 & 25° C.: | | | | | | | | |
|---|---|---|---|---|---|---|---|---|
| Temp. error (° C.) | 8256 | 8256 | 8256 | AVG | 9256 | 9256 | 9256 | AVG |
| Max | 0.14 | 0.02 | 0.13 | 0.10 | 0.08 | 0.26 | 0.31 | 0.22 |
| Mean | 0.04 | 0.01 | 0.05 | 0.03 | 0.03 | 0.09 | 0.11 | 0.08 |
| Std Dev | 0.06 | 0.01 | 0.05 | 0.04 | 0.04 | 0.13 | 0.12 | 0.10 |

| Calibrated at 20, 25 & 40° C.: | | | | | | | | |
|---|---|---|---|---|---|---|---|---|
| Temp. error (° C.) | 9202 | 9202 | 9202 | AVG | 9206 | 9206 | 9206 | AVG |
| Max | 0.16 | 0.14 | 0.05 | 0.12 | 0.04 | 0.27 | 0.04 | 0.12 |
| Mean | 0.05 | 0.08 | 0.02 | 0.05 | 0.02 | 0.11 | 0.01 | 0.05 |
| Std Dev | 0.06 | 0.06 | 0.03 | 0.05 | 0.01 | 0.14 | 0.02 | 0.06 |

TABLE 11

| Calibrated at 20, 25 & 40° C.: | | | | | | | | |
|---|---|---|---|---|---|---|---|---|
| Temp. error (° C.) | 8272 | 8272 | 8272 | AVG | 9272 | 9272 | 9272 | AVG |
| Max | 0.00 | 0.05 | 0.06 | 0.04 | 0.02 | 0.01 | 0.01 | 0.01 |
| Mean | 0.00 | 0.01 | 0.02 | 0.01 | 0.01 | 0.00 | 0.00 | 0.00 |
| Std Dev | 0.00 | 0.02 | 0.03 | 0.02 | 0.01 | 0.00 | 0.00 | 0.00 |
| Calibrated at 20, 25 & 40° C.: | | | | | | | | |
| Temp. error (° C.) | 9203 | 9203 | 9203 | AVG | 8202 | 8202 | 8202 | AVG |
| Max | 0.32 | 0.17 | 0.23 | 0.24 | 0.09 | 0.08 | 0.23 | 0.13 |
| Mean | 0.13 | 0.05 | 0.06 | 0.08 | 0.03 | 0.03 | 0.07 | 0.04 |
| Std Dev | 0.15 | 0.07 | 0.09 | 0.11 | 0.03 | 0.04 | 0.09 | 0.05 |
| Calibrated at 20, 25 & 40° C.: | | | | | | | | |
| Temp. error (° C.) | 8256 | 8256 | 8256 | AVG | 9256 | 9256 | 9256 | AVG |
| Max | 0.42 | 0.38 | 0.41 | 0.40 | 0.36 | 0.30 | 0.42 | 0.36 |
| Mean | 0.09 | 0.08 | 0.09 | 0.09 | 0.06 | 0.13 | 0.09 | 0.09 |
| Std Dev | 0.17 | 0.15 | 0.15 | 0.16 | 0.14 | 0.18 | 0.16 | 0.16 |

TABLE 14

| Calibrated at 25° C. and checked in 20 to 30° range: | | | | | | | | |
|---|---|---|---|---|---|---|---|---|
| Temp. error (° C.) | 9202 | 9202 | 9202 | AVG | 9206 | 9206 | 9206 | AVG |
| Max | 0.30 | 0.62 | 0.24 | 0.39 | 0.36 | 0.33 | 0.21 | 0.30 |
| Mean | 0.21 | 0.32 | 0.16 | 0.23 | 0.21 | 0.17 | 0.12 | 0.17 |
| Std Dev | 0.24 | 0.38 | 0.18 | 0.27 | 0.25 | 0.15 | 0.14 | 0.18 |
| Calibrated at 25° C. and checked in 20 to 30° range: | | | | | | | | |
| Temp. error (° C.) | 8272 | 8272 | 8272 | AVG | 9272 | 9272 | 9272 | AVG |
| Max | 0.75 | 0.79 | 0.31 | 0.62 | 0.24 | 0.06 | 0.17 | 0.16 |
| Mean | 0.45 | 0.49 | 0.22 | 0.39 | 0.15 | 0.05 | 0.10 | 0.10 |
| Std Dev | 0.54 | 0.58 | 0.25 | 0.46 | 0.17 | 0.05 | 0.11 | 0.11 |
| Calibrated at 10° C. and checked in 0 to 20° range: | | | | | | | | |
| Temp. error (° C.) | 9202 | 9202 | 9202 | AVG | 9206 | 9206 | 9266 | AVG |
| Max | 0.72 | 1.24 | 4.67 | 2.21 | 0.57 | 4.52 | 1.70 | 2.26 |
| Mean | 0.27 | 0.79 | 2.18 | 1.08 | 0.21 | 2.05 | 0.70 | 0.99 |
| Std Dev | 0.36 | 0.95 | 2.74 | 1.35 | 0.27 | 2.59 | 0.91 | 1.26 |

TABLE 12

The data was next analyzed using the system defaults for variables A & B and a one point calibration

| Temp. error (° C.) | 8235 | 9207 | 8202 | 8272 | 8256 | 9256 | 9202 | 9203 | 9206 | 9272 | AVG |
|---|---|---|---|---|---|---|---|---|---|---|---|
| Calibrated at 25° C. and checked in 20 to 30° range: | | | | | | | | | | | |
| Max | 1.52 | 0.65 | 0.19 | 0.03 | 0.13 | 0.40 | 0.59 | 0.21 | 0.12 | 0.05 | 0.43 |
| Avg | 0.91 | 0.38 | 0.13 | 0.03 | 0.09 | 0.22 | 0.33 | 0.12 | 0.06 | 0.04 | 0.24 |
| Std | 1.11 | 0.45 | 0.15 | 0.00 | 0.10 | 0.26 | 0.39 | 0.13 | 0.07 | 0.04 | 0.29 |
| Temp. Error (° C.) | AVG | | | | | | | | | | |
| Max | 0.39 | | | | | | | | | | |
| Mean | 0.23 | | | | | | | | | | |
| Std Dev | 0.27 | | | | | | | | | | |
| Calibrated at 10° C. and checked in 0 to 20° range: | | | | | | | | | | | |
| Max | 5.08 | 4.14 | 2.77 | 0.37 | 0.26 | 1.87 | 1.56 | 0.25 | 2.91 | 2.19 | 2.18 |
| Avg | 3.32 | 3.57 | 2.52 | 0.30 | 0.18 | 1.65 | 0.98 | 0.17 | 1.23 | 1.03 | 1.16 |
| Std | 4.05 | 0.51 | 0.20 | 0.06 | 0.06 | 0.22 | 1.19 | 0.13 | 1.58 | 1.29 | 1.43 |
| Temp. Error (° C.) | AVG | | | | | | | | | | |
| Max | 2.14 | | | | | | | | | | |
| Mean | 1.46 | | | | | | | | | | |
| Std Dev | 0.97 | | | | | | | | | | |

TABLE 13

| Calibrated at 40° C. and checked in 30 to 50° range | | | | | | | | | | | |
|---|---|---|---|---|---|---|---|---|---|---|---|
| Temp. error (° C.) | 8235 | 9207 | 8202 | 8272 | 8256 | 9256 | 9202 | 9203 | 9206 | 9272 | AVG |
| Max | 1.71 | 0.58 | 0.10 | 0.19 | 0.18 | 0.32 | 0.43 | 0.32 | 0.17 | 0.12 | 0.31 |
| Avg | 0.95 | 0.27 | 0.07 | 0.12 | 0.10 | 0.12 | 0.22 | 0.21 | 0.10 | 0.08 | 0.17 |
| Std | 1.17 | 0.33 | 0.07 | 0.07 | 0.06 | 0.14 | 0.27 | 0.24 | 0.06 | 0.09 | 0.19 |
| Temp. Error (° C.) | AVG | | | | | | | | | | |
| Max | 0.41 | | | | | | | | | | |
| Mean | 0.22 | | | | | | | | | | |
| Std Dev | 0.24 | | | | | | | | | | |

TABLE 15

Calibrated at 10° C. and checked in 0 to 20° range:

| Temp. error (° C.) | 8272 | 8272 | 8272 | AVG | 9272 | 9272 | 9272 | AVG |
|---|---|---|---|---|---|---|---|---|
| Max | 1.54 | 1.95 | 1.04 | 1.51 | 0.31 | 2.60 | 1.19 | 1.37 |
| Mean | 1.00 | 1.26 | 0.44 | 0.90 | 0.20 | 1.15 | 0.42 | 0.59 |
| Std Dev | 1.22 | 1.53 | 0.45 | 1.07 | 0.15 | 1.46 | 0.58 | 0.73 |

Calibrated at 40° C. and checked in 30 to 50° range:

| Temp. error (° C.) | 9202 | 9202 | 9202 | AVG | 9206 | 9206 | 9206 | AVG |
|---|---|---|---|---|---|---|---|---|
| Max | 0.25 | 0.48 | 0.25 | 0.33 | 0.40 | 0.22 | 0.24 | 0.29 |
| Mean | 0.11 | 0.26 | 0.08 | 0.15 | 0.21 | 0.07 | 0.14 | 0.14 |
| Std Dev | 0.11 | 0.25 | 0.12 | 0.16 | 0.19 | 0.09 | 0.08 | 0.12 |

TABLE 15-continued

Calibrated at 40° C. and checked in 30 to 50° range:

| Temp. error (° C.) | 8272 | 8272 | 8272 | AVG | 9272 | 9272 | 9272 | AVG |
|---|---|---|---|---|---|---|---|---|
| Max | 0.79 | 0.72 | 0.40 | 0.64 | 0.39 | 0.09 | 0.22 | 0.23 |
| Mean | 0.32 | 0.34 | 0.18 | 0.28 | 0.16 | 0.07 | 0.13 | 0.12 |
| Std Dev | 0.40 | 0.42 | 0.21 | 0.34 | 0.20 | 0.07 | 0.15 | 0.14 |

Test data for the following nine models (one each) of electrodes (Orion Model Nos. 8202, 8235, 8256, 8272, 9202, 9203, 9206, 9207 and 9256) were obtained and evaluated at 15 temperatures, ranging from 0–90° C. Using a 2 point calibrations at various temperatures for the A & C values, the following results (Tables 16–18) were obtained in comparing the calculated temperature to the thermistor measured values.

TABLE 16

| Temp. error (° C.) | 8235 | 9207 | 8202 | 8272 | 8256 | 9256 | 9202 | 9203 | 9206 | AVG |
|---|---|---|---|---|---|---|---|---|---|---|
| Calibrated at 0 & 90° C.: | | | | | | | | | | |
| Max | 1.43 | 1.19 | 1.15 | 0.69 | 1.20 | 1.50 | 1.65 | 1.21 | 0.83 | 1.20 |
| Mean | 0.37 | 0.62 | 0.36 | 0.35 | 0.55 | 0.73 | 0.79 | 0.57 | 0.46 | 0.53 |
| Std Dev | 0.54 | 0.43 | 0.49 | 0.20 | 0.36 | 0.57 | 0.56 | 0.52 | 0.49 | 0.46 |
| Calibrated at 10 & 60° C.: | | | | | | | | | | |
| Max | 0.89 | 0.47 | 0.51 | 0.31 | 0.52 | 0.32 | 0.46 | 0.93 | 0.52 | 0.55 |
| Mean | 0.51 | 0.26 | 0.20 | 0.18 | 0.20 | 0.15 | 0.14 | 0.49 | 0.19 | 0.26 |
| Std Dev | 0.30 | 0.20 | 0.21 | 0.11 | 0.19 | 0.17 | 0.18 | 0.31 | 0.24 | 0.21 |
| Calibrated at 20 & 60° C.: | | | | | | | | | | |
| Max | 0.55 | 0.45 | 0.23 | 0.18 | 0.09 | 0.36 | 0.47 | 0.73 | 0.37 | 0.38 |
| Mean | 0.35 | 0.25 | 0.09 | 0.10 | 0.05 | 0.09 | 0.16 | 0.31 | 0.15 | 0.17 |
| Std Dev | 0.21 | 0.18 | 0.10 | 0.08 | 0.05 | 0.13 | 0.17 | 0.25 | 0.15 | 0.15 |

TABLE 17

| Temp. error (° C.) | 8235 | 9207 | 8202 | 8272 | 8256 | 9256 | 9202 | 8203 | 9206 | AVG |
|---|---|---|---|---|---|---|---|---|---|---|
| Calibrated at 10 & 50° C.: | | | | | | | | | | |
| Max | 0.65 | 0.29 | 0.57 | 0.25 | 0.51 | 0.40 | 0.29 | 0.78 | 0.61 | 0.48 |
| Mean | 0.32 | 0.17 | 0.24 | 0.12 | 0.22 | 0.20 | 0.13 | 0.41 | 0.21 | 0.22 |
| Std Dev | 0.22 | 0.15 | 0.22 | 0.09 | 0.19 | 0.17 | 0.15 | 0.26 | 0.23 | 0.19 |
| Calibrated at 20 & 50° C.: | | | | | | | | | | |
| Max | 0.39 | 0.28 | 0.14 | 0.12 | 0.09 | 0.19 | 0.26 | 0.58 | 0.18 | 0.25 |
| Mean | 0.19 | 0.19 | 0.07 | 0.07 | 0.06 | 0.09 | 0.12 | 0.24 | 0.08 | 0.12 |
| Std Dev | 0.14 | 0.14 | 0.08 | 0.07 | 0.06 | 0.11 | 0.15 | 0.22 | 0.09 | 0.12 |
| Calibrated at 10 & 40° C.: | | | | | | | | | | |
| Max | 0.51 | 0.14 | 0.60 | 0.24 | 0.54 | 0.31 | 0.20 | 0.28 | 0.62 | 0.38 |
| Mean | 0.24 | 0.06 | 0.30 | 0.12 | 0.27 | 0.12 | 0.09 | 0.12 | 0.28 | 0.18 |
| Std Dev | 0.18 | 0.07 | 0.22 | 0.09 | 0.19 | 0.10 | 0.10 | 0.14 | 0.22 | 0.15 |

TABLE 18

| Temp. error (° C.) | 8235 | 9207 | 8202 | 8272 | 8256 | 9256 | 9202 | 9203 | 9206 | AVG |
|---|---|---|---|---|---|---|---|---|---|---|
| Calibrated at 20 & 40° C.: | | | | | | | | | | |
| Max | 0.33 | 0.16 | 0.23 | 0.13 | 0.16 | 0.06 | 0.23 | 0.18 | 0.14 | 0.18 |
| Mean | 0.14 | 0.07 | 0.10 | 0.08 | 0.09 | 0.03 | 0.09 | 0.11 | 0.07 | 0.09 |
| Std Dev | 0.13 | 0.07 | 0.08 | 0.08 | 0.05 | 0.04 | 0.11 | 0.13 | 0.06 | 0.08 |
| Calibrated at 0 & 25° C.: | | | | | | | | | | |
| Max | 0.05 | 0.29 | 0.92 | 0.48 | 0.74 | 0.63 | 0.47 | 0.52 | 0.71 | 0.53 |
| Mean | 0.04 | 0.16 | 0.35 | 0.22 | 0.31 | 0.27 | 0.22 | 0.26 | 0.31 | 0.24 |
| Std Dev | 0.04 | 0.13 | 0.37 | 0.19 | 0.30 | 0.25 | 0.19 | 0.23 | 0.29 | 0.22 |

In addition, each electrode was tested at 2 temperatures in 3 different buffers (4, 7 & 10). The results show that the Log R temperature response was unaffected by pH.

The present invention has been described in detail, including the preferred embodiments thereof. However, it will be appreciated that those skilled in the art, upon consideration of the present disclosure, may make modifications and/or improvements on this invention and still be within the scope and spirit of this invention as set forth in the following claims.

What is claimed is:

1. In a method of improving the measurement accuracy of an electrochemical meter connected to an electrochemical sensor membrane electrode, said meter utilizing resistance-responsive circuitry to implement the following log R algorithm to compensate for temperature changes in the electrode environment:

$$1/T = A \times \ln(R) + B$$

wherein T is the temperature in ° K., R is the membrane resistance, A is 0.000099 and B is 0.11964;
the improvement comprising the steps of:
(a) establishing a target resistance-temperature (R-T) calibration curve as a function of the calibration curves of a plurality of sensor membranes found to have a desirable R-T characteristic shape;
(b) adding a linear resistance term to the log R algorithm to correct the calculated temperature measurement made using the sensor membrane resistance to provide a linearized compensation factor across a wide temperature range, thereby changing the log R algorithm to the following:

$$1000/T = A \times R + B \times \ln(R) + C$$

wherein T is the temperature in ° K., R is the membrane resistance, A is 0.000099, B is 0.11964 and C is 2.652662;
(c) presetting the resistance-responsive circuitry of the electrochemical meter for response to the target R-T calibration curve; and
(d) providing a microprocessor for calibrating the resistance-responsive circuitry to increase the accuracy and compensate for a wide variety of sensor membranes.

2. The method of claim 1, wherein the meter further includes a switched reference and switched capacitor filter to eliminate hardware drift.

3. The method of claim 1, wherein a microprocessor is used to control and measure the resistance-responsive circuitry.

4. The method of claim 1, wherein a microprocessor is used to eliminate hardware calibration.

5. The method of claim 1, wherein a microprocessor is used to implement one or more temperature measurement algorithms or calibration procedures based on the sensor membrane resistance.

6. The method of claim 1, wherein the meter further comprises a thermistor temperature measurement circuit.

7. The method of claim 1, wherein the meter further comprises a switch to turn off the log R algorithm.

8. Improved ion measurement apparatus comprising:
(a) an ion probe for measuring the ion activity of a solution;
(b) means for measuring the direct current potential across the ion probe;
(c) means for measuring the electrical resistance of the ion probe;
(d) resistance-response circuitry including electronic means for determining from the said two measuring means the ion activity of said solution corrected for the temperature thereof;
(e) a microprocessor for implementing temperature correction of the apparatus by the following modified log R algorithm:

$$1000/T = A \times R + B \times \ln(R) + C$$

wherein T is the temperature in ° K, R is the membrane resistance, A is 0.000099, B is 0.11964 and C is 2.652662; to correct a calculated temperature measurement made using the ion probe resistance, thereby providing a linearized compensation factor across a wide temperature range.

9. The ion measurement apparatus of claim 8, further comprising a switched reference and switched capacitor filter to eliminate hardware drift.

10. The ion measurement apparatus of claim 8, further comprising a microprocessor to eliminate hardware calibration.

11. The ion measurement apparatus of claim 8, further comprising a microprocessor to implement one or more temperature measurement algorithms or calibration procedures based on the ion probe resistance.

12. The ion measurement apparatus of claim 8, further comprising a thermistor temperature measurement circuit.

13. The ion measurement apparatus of claim 8, further comprising a switch to turn off the log R algorithm.

14. The improved ion measurement apparatus of claims 8, wherein said ion probe includes a glass membrane electrode.

15. The improved ion measurement apparatus of claim 8, wherein said ion probe is a pH probe.

16. The improved ion measurement apparatus of claim 8, wherein said ion probe includes a sodium electrode.

17. The improved ion measurement apparatus of claims 8, wherein said electronic means include means for reading said solution temperature directly.

* * * * *